United States Patent [19]

Cihonski

[11] 4,210,603

[45] Jul. 1, 1980

[54] PRODUCTION OF CYCLIC HYDROCARBONS FROM N-BUTENES

[75] Inventor: John L. Cihonski, Odessa, Tex.

[73] Assignee: El Paso Products Company, Odessa, Tex.

[21] Appl. No.: 30,539

[22] Filed: Apr. 16, 1979

[51] Int. Cl.² .................. C07C 85/11; C07C 15/10; C07C 3/44
[52] U.S. Cl. .................. 260/580; 585/365; 585/414; 585/418; 585/419; 585/435
[58] Field of Search ............... 260/580; 585/414, 418, 585/419, 365

[56] References Cited

U.S. PATENT DOCUMENTS

| | | | |
|---|---|---|---|
| 2,376,985 | 5/1945 | Voorhees | 585/419 |
| 2,392,960 | 1/1946 | Watson | 585/419 |
| 3,308,193 | 3/1967 | Bajars | 585/418 |
| 4,056,575 | 7/1976 | Gregory et al. | 585/365 |

FOREIGN PATENT DOCUMENTS

281455 12/1970 U.S.S.R. ................... 260/580

OTHER PUBLICATIONS

Csicsery, "J. of Catalysts", vol. 17, pp. 207–215, 216–218, 315–322, & 323–330, (1970).
Csicsery, "J. of Catalysts", vol. 18, pp. 30–32, (1970).

*Primary Examiner*—John Doll

[57] ABSTRACT

This invention provides a process for the production of cyclic hydrocarbons for light olefinic hydrocarbons which involves contacting n-butenes with a Group VIII metal oxide catalyst in the presence of molecular oxygen at temperatures of 130°–500° C. and a pressure of 1–200 psi to yield vinylcyclohexene and ethylbenzene with a selectivity of at least 80 weight percent.

The invention further provides a two step vapor phase process embodiment for converting n-butenes to styrene via a vinylcyclohexene/ethylbenzene intermediate mixture. When nitrobenzene is employed as the oxidizing agent in place of molecular oxygen, aniline is obtained as an additional product.

6 Claims, No Drawings

PRODUCTION OF CYCLIC HYDROCARBONS FROM N-BUTENES

BACKGROUND OF THE INVENTION

Light petroleum fractions from refinery and petrochemical operations constitute a potentially valuable raw material source for the production of styrene and other commercially important aromatic compounds.

Processes for the conversion of light paraffins to aromatic hydrocarbons at some stage usually involve naphthenic compounds. A well-known reaction is the dehydrocyclization of $C_6$ and higher paraffins to aromatic derivatives containing the same number or less carbon atoms than the feed material.

More recent development efforts have been concerned with a dehydrocyclodimerization mechanism of reaction, wherein a light olefinic hydrocarbon such as butadiene is dimerized to vinyl cyclohexene, which intermediate is subsequently sujected to catalytic dehydrogenation conditions to yield product mixtures of aromatic compounds such as benzenes, ethylbenzene, xylene, styrene, methylstyrene, naphthalene, and the like.

Efforts to develop economical processes for selective production of styrene from readily available hydrocarbon raw materials have encountered many difficulties. Several prior art methods have been advanced which address the most serious of the technical problems.

U.S. Pat. No. 2,376,985 describes a two-step process for converting butadiene to styrene. In the first step, butadiene is heated at 250°–500° C. under 1–10 atomspheres pressure preferably in the presence of a catalyst such as chromium oxide or silica gel to form butadiene dimer. In the second step, the butadiene dimer is automized in the presence of a Group V, VI or VIII metal catalyst. The second step is conducted at a temperature of 450°–800° C. and pressure of 0.2–2 atmospheres for a reaction period of 0.1–100 seconds.

U.S. Pat. No. 2,392,960 describes a cyclic process for the production of styrene which involves (1) subjecting a butane-butene-butadiene feed to a temperature of 650°–950° C. under superatmospheric pressure to effect dimerization of the butadiene component, and (2) contacting the resultant effluent from the first step with chromium or molybdenum metal catalyst at a temperature of 1200°–1400° F. and a pressure of 1 atmosphere for a 0.001–0.1 second reaction time to yield styrene. A proportion of the butane and butene components of the reaction mixture are converted to butadiene during the dehydrogenation step and recycled to the first step of the process.

U.S. Pat. No. 2,438,041 describes a process for producing styrene which comprises (1) contacting butadiene at 150°–480° C. and 20–30 atmospheres with a catalyst selected from Fuller's earth, bauxite, alumina and silica gel to form an effluent which contains butadiene dimer, (2) separating tar from the effluent, and (3) dehydrogenating the butadiene dimer component of the effluent over a chromium oxide on alumina catalyst at a temperature of 400°–600° C. and a pressure of at least 1 atmosphere. In the illustrated Example, the resultant product mixture contained 13.8 weight percent of styrene and 5.3 percent ethylbenzene.

U.S. Pat. No. 3,502,736 describes on improved method for oxidative dehydrogenation of alkenylnaphthenes to alkenylaryl compounds. A non-aromatic cyclic hydrocarbon having at least one unsaturated bond in a sidechain (e.g., vinylcyclohexene) is contacted with a palladium oxyhydrate catalyst in the presence of oxygen to yield the corresponding alkenylaryl derivative (e.g., styrene).

S.M. Csicsery reports extensive dehydrocyclodimerization studies in a I-V series of articles in the Journal of Catalysis [17, 207, 216, 315, 323; 18, 30 (1970)]. $C_3$–$C_5$ paraffins were converted in one step to aromatics at temperatures over 430° C. in the presence of dual-functioning catalyst having dehydrogenation and acid-type activities (e.g., platinum on acidic alumina). The products from butanes were principally xylene and toluene. Ethylbenzene and styrene were the predominant $C_8$ aromatics formed from n-butane over weakly acidic catalysts. Dehydrocyclodimerization of propane over supported platinum catalysts produced benzene as the principle aromatic product, and pentane yielded naphthalenes and other condensed aromatics. At very short contact times over Pt-alumina catalysts butenes converted to $C_5$–$C_8$ olefins and naphthenes in large proportion, which suggested that these compounds were intermediates in butene aromatization. In Paper V it is theorized that dehydrocyclodimerization proceeds by (1) conversion of the light paraffins to monoolefins and diolefins, (2) dimerization of the olefins, (3) aromatization of the dimerized olefins, and (4) the isomerization, transalkylation and dealkylation of the primary aromatics to produce a large number of $C_8$–$C_{10}$ alkylbenzene isomers.

There remains a need for improved methods for converting low value light hydrocarbon overhead streams from petroleum refinery operations into more valuable derivatives such as naphthenes and aromatic hydrocarbons.

Accordingly, it is an object of this invention to provide an improved process for converting light acyclic hydrocarbons into cyclic hydrocarbons.

It is another object of this invention to provide an improved process for converting n-butenes into naphthenes and aromatic hydrocarbons.

It is a further object of this invention to provide an improved two-step process for converting n-butenes into styrene.

Other objects and advantages shall become apparent from the following description and examples.

DESCRIPTION OF THE INVENTION

One or more objects of the present invention are accomplished by the provision of a process for the production of cyclic hydrocarbons from light acyclic hydrocarbons which comprises contacting n-butenes with an oxidized Group VIII metal catalyst in the presence of molecular oxygen at a temperature between about 130° C. and 500° C. and a pressure between about 1 and 200 psi to convert the n-butenes to vinylcyclohexene and ethylbenzene with a conversion efficiency of at least 80 weight percent. The reaction can be conducted as a batch or continuous process, either in the liquid or vapor phase. As a liquid phase reaction, the process is preferably conducted at a temperature between about 130° C. and 300° C. for a reaction period between about 1 and 10 hours.

In a preferred embodiment, this invention provides a vapor phase process for the production of styrene from light hydrocarbons which comprises the steps of (1) contacting n-butene with a Group VIII metal oxide or hydroxide catalyst in the presence of molecular oxygen at a temperature between about 130° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a Group VIII metal oxide or hydroxide catalyst in the presence of molecular oxygen at a temperature between about 150° C. and 300° C. and a pressure between about 1 and 200 psi for a residence time between about 0.1 and 10 seconds to yield styrene product.

The n-butene feedstock can be either 1-butene or 2-butene, or a mixture thereof. This invention also contemplates the use of feedstocks which are mixtures of n-butene with other light acyclic hydrocarbons such as butane, isobutane, isobutylene, butadiene, n-octenes and the like. Butane, butadiene and n-octenes are susceptible to conversion to vinylcyclohexene and ethylbenzene under the conditions of the present invention process.

Suitable reactors for the vapor phase conversion of n-butene include either fixed bed or fluid bed reactors which contain at least one Group VIII metal oxide or hydroxide catalyst component. The gas fed to the reactors comprises n-butene and molecular oxygen to which nitrogen, carbon dioxide, steam or the like may optionally be added as an inert diluent. Unreacted n-butene feed can be recycled in the process if desired.

In the two-step vapor phase process for styrene production described above, the first step reaction is conducted at temperatures between about 130° C. and 500° C., and preferably at a temperature between about 150° C. and 300° C. The residence time (i.e., catalyst contact time) of the feed stream in the first step reaction is between about 0.5 and 20 seconds, and preferably between about 1 and 15 seconds. Residence time refers to the contact time adjusted to 25° C. and atmospheric pressure. The contact time is calculated by dividing the volume of the catalyst bed (including voids) by the volume per unit time flow rate of the feed stream at NTP.

The mixture containing vinylcyclohexene and ethylbenzene which is the effluent from the first step reaction zone can be introduced directly into the second step reaction zone without any fractionation of effluent components. If desired, the vinylcyclohexene and ethylbenzene can be separated from the other components of the effluent mixture in an essentially pure state. The vinylcyclohexene and ethylbenzene can then be vaporized, admixed with molecular oxygen, and entered into the second step reaction zone to produce the product styrene.

The pressure utilized in the two step vapor phase process can be subatmospheric, atmospheric or superatmospheric. A preferred pressure for the vapor phase process is one which is in the range between about 1 and 200 psi.

In any of the embodiments of the present invention process, the quantity of molecular oxygen (or its equivalent) introduced into the dehydrocyclodimerization reaction system theoretically should be at least sufficient to satisfy the stoichiometry of the oxidative conversions. The molar ratio of oxygen to n-butene feed can vary broadly over the range between about 0.1:1 and 10:1. A molar ratio of oxygen to n-butene of about 1:1 has been found to be convenient and effective.

It is not necessary to use pure oxygen as the source of oxygen. Air is a suitable source of oxygen and is desirable for reasons of economy. Alternatively, the oxidizing agent can be ozone (under conditions which prevent direct interaction of ozone and olefin) or a compound which can generate oxygen under reaction conditions (e.g., peroxides and hydroperoxides), or it can be a compound which contains an active-oxygen functional group (e.g., nitro derivatives). Aliphatic and aromatic nitro compounds which have a boiling point below about 250° C. are particularly useful as an oxidizing agent in place of molecular oxygen in the invention process. Thus, in another embodiment this invention provides a process for the production of styrene and aniline which comprises contacting n-butenes with a Group VIII metal oxide or hydroxide catalyst in the presence of nitrobenzene at a temperature between about 200° C. and 500° C. and a pressure between about 1 and 200 psi to yield styrene and aniline product.

In a more preferred embodiment, this invention provides a vapor phase process for the production of styrene and aniline which comprises contacting n-butene with a Group VIII metal oxide or hydroxide catalyst in the presence of molecular oxygen at a temperature between about 200° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a Group VIII metal oxide or hydroxide catalyst in the presence of nitrobenzene at a temperature between about 200° C. and 300° C. and a pressure between about 1 and 200 psi for a residence time between about 0.1 and 10 seconds to yield styrene and aniline product.

The catalyst employed in the invention process is selected from one or more Group VIII metals which are in an oxidized state (e.g., an oxide or a hydroxide). The preferred Group VIII metals are nickel, palladium and platinum, with palladium being the most preferred Group VIII metal species.

The catalyst can be prepared by adding an alkali (e.g., sodium or potassium hydroxide) to a solution of one or more water soluble Group VIII metal compounds, such as the chlorides, nitrates and sulfates of nickel, palladium and platinum. The precipitate which forms is recovered, washed with water, and dried.

It has been found that the activity of the catalyst is enhanced if the prepared catalyst is calcined in air at a temperature between about 250° C. and 500° C. for a period of about 1–24 hours.

The Group VIII metal oxide or hydroxide composition described can be used as the catalyst per se, but it is preferred that the said composition is combined with a suitable internal diluent or carrier substrate.

The carrier substrate should be relatively refractory to the conditions utilized in the invention process. Suitable carrier substrate materials include (1) silica or silica gel, silicon carbide, clays, and silicates including those synthetically prepared and naturally occurring, which may or may not be acid treated such as attapulgus clay, china clay, diatomaceous earth, Fuller's earth, kaolin, asbestos and kieselguhr; (2) ceramics, porcelain, crushed firebrick and bauxite; (3) refractory inorganic oxides such as alumina, titanium dioxide, zirconium dioxide, chromium oxide, beryllium oxide, vanadium oxide, cesium oxide, hafnium oxide, zinc oxide, molybdenum oxide, bismuth oxide, tungsten oxide, uranium oxide, magnesia, boria, thoria, silica-alumina, silica-magnesia, chromia-alumina, alumina-boria and silica-zirconia; (4) crystalline zeolitic alumino-silicates such as naturally occurring or synthetically prepared mordenite and/or faujasite, either in the hydrogen form or in a form which has been treated with multivalent cations; and (5) spinels such as $MgAl_2O_4$, $FeAl_2O_4$, $ZnAl_2O_4$, $MnAl_2O_4$, $CaAl_2O_4$, and other like compounds having the formula $MO.Al_2O_3$ where M is a metal having a valence of 2.

The catalyst as employed in the invention process can be in the shape of granules, pellets, extrudate, powders, tablets, fibers, or other such convenient physical form.

The following examples are further illustrative of the present invention. The reactants and other specific ingredients are presented as being typical, and various modifications can be derived in view of the foregoing disclosure within the scope of the invention.

EXAMPLE I

To a solution of 20 grams of palladium chloride in 100 milliliters of 0.5 N hydrochloric acid and 400 milliliters of water, is added 100 grams of asbestos and a quantity of 0.5 N sodium hydroxide solution equivalent to the amount of chloride present in the resultant admixture. After a 30 minute refluxing period, the precipitate is separated by filtration, washed with water, and dried at 200° C. for 24 hours.

The recovered catalyst is calcined in air at a temperature of 300° C. for 24 hours, and then crushed and sieved to yield 20–30 mesh catalyst particles. About 5 $cm^3$ of the catalyst composition are blended with about 10 $cm^3$ mesh crushed fused quartz and charged into a 7 mm I.D. glass tube reactor.

A gaseous feed is prepared by admixing 1-butene and air in proportions which provide about a 1:1 molar ratio of 1-butene to molecular oxygen.

The feed mixture is passed through the tube reactor at a temperature of about 250° C. under autogenous pressure at a rate providing a catalyst contact time of about 10 seconds.

The conversion of 1-butene per single pass is 18 percent and the conversion efficiency (i.e., selectivity), based on the total weight of liquid product, is 67 weight percent vinylcyclohexene, 27 percent weight percent ethylbenzene, and 6 weight percent styrene.

The liquid product mixture is vaporized and mixed with air in about a 1:1 molar ratio of hydrocarbons to molecular oxygen, and passed through a tube reactor containing the same type of palladium on asbestos catalyst described above.

The second step dehydrogenation reaction is conducted at a temperature of about 215° C. under autogenous pressure with a contact time of about 5 seconds.

The average single pass conversion of ethylbenzene and vinylcyclohexene is in the range of 15–25 percent, and the resultant product mixture consists mainly of unreacted vinylcyclohexene and ethylbenzene, and it contains styrene as the sole product of the conversion reaction.

EXAMPLE II

Following the same procedure and employing the same type of catalyst system as described in Example I, a mixture of n-butenes is dehydrocyclodimerized to styrene employing nitrobenzene as the oxidizing component instead of molecular oxygen.

The n-butenes consist of approximately a 1:1 molar ratio of 1-butene/2-butene. The nitrobenzene is employed in an approximately equimolar quantity relative to the n-butenes.

The palladium on asbestos catalyst bed in the reactor is divided into two zones. In the first zone the temperature is maintained in the range of 250°–300° C., and in the second zone the temperature is maintained in the range of 200°–250° C. The contact time in each zone is about 10 seconds.

The average conversion of n-butenes is about 10 percent per single pass. The resultant liquid product mixture consists of about 45 weight percent each of styrene and aniline and 10 weight percent of byproducts, exclusive of unreacted nitrobenzene.

In a preferred embodiment, molecular oxygen is employed as the oxidizing agent in the first step of the process, and nitrobenzene is used in the second step without the presence of molecular oxygen.

What is claimed is:

1. A process for the production of cyclic hydrocarbons from light acyclic hydrocarbons which comprises contacting n-butenes with an oxidized Group VIII metal catalyst in the presence of molecular oxygen at a temperature between about 130° C. and 500° C. and a pressure between about 1 and 200 psi to convert the n-butenes to vinylcyclohexene and ethylbenzene with a conversion efficiency of at least 80 weight percent.

2. A process in accordance with claim 1 wherein the Group VIII metal catalyst is selected from palladium, platinum and nickel oxides and hydroxides.

3. A process in accordance with claim 1 wherein the Group VIII metal catalyst is supported on a carrier substrate.

4. A vapor phase process for the production of styrene from light hydrocarbons which comprises the steps of (1) contacting n-butene with a Group VIII metal oxide or hydroxide catalyst in the presence of molecular oxygen at a temperature between about 130° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a Group VIII metal oxide or hydroxide catalyst in the presence of molecular oxygen at a temperature between about 150° C. and 300° C. and a pressure between about 1 and 200 psi for a residence time between about 0.1 and 10 seconds to yield styrene product.

5. A process for the production of styrene and aniline which comprises contacting n-butenes with a Group VIII metal oxide or hydroxide catalyst in the presence of nitrobenzene at a temperature between about 200° C. and 500° C. and a pressure between about 1 and 200 psi to yield styrene and aniline product.

6. A vapor phase process for the production of styrene and aniline which comprises contacting n-butene with a Group VIII metal oxide or hydroxide catalyst in the presence of molecular oxygen at a temperature between about 200° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a Group VIII metal oxide or hydroxide catalyst in the presence of nitrobenzene at a temperature between about 200° C. and 300° C. and a pressure between about 1 and 200 psi for a residence time between about 0.1 and 10 seconds to yield styrene and aniline product.

* * * * *